United States Patent
Steingisser et al.

(10) Patent No.: US 9,808,629 B2
(45) Date of Patent: Nov. 7, 2017

(54) DELIVERY SYSTEM ASSEMBLIES AND ASSOCIATED METHODS FOR IMPLANTABLE MEDICAL DEVICES

(71) Applicant: Medtronic, Inc., Minneapolis, MN (US)

(72) Inventors: H. Allan Steingisser, Santa Rosa, CA (US); Don H. Tran, Novato, CA (US); William A. Berthiaume, Santa Rosa, CA (US); Brent L. Locsin, San Francisco, MN (US)

(73) Assignee: Medtronic, Inc., Minneapolis, MN (US)

( * ) Notice: Subject to any disclaimer, the term of this patent is extended or adjusted under 35 U.S.C. 154(b) by 66 days.

(21) Appl. No.: 14/611,582

(22) Filed: Feb. 2, 2015

(65) Prior Publication Data

US 2015/0148815 A1 May 28, 2015

Related U.S. Application Data

(62) Division of application No. 13/279,835, filed on Oct. 24, 2011, now Pat. No. 8,945,146.

(51) Int. Cl.
*A61B 19/00* (2006.01)
*A61N 1/372* (2006.01)
(Continued)

(52) U.S. Cl.
CPC ....... *A61N 1/37205* (2013.01); *A61N 1/3756* (2013.01); *A61N 1/3622* (2013.01); *A61N 2001/0578* (2013.01)

(58) Field of Classification Search
CPC .............. A61N 1/37205; A61N 1/3756; A61N 2001/0578; A61N 1/3622
(Continued)

(56) References Cited

U.S. PATENT DOCUMENTS 3,835,864 A 9/1974 Rasor et al.
3,943,936 A 3/1976 Rasor et al.
(Continued)

FOREIGN PATENT DOCUMENTS

CN 1870950 A 11/2006
CN 101779992 A 7/2010
(Continued)

OTHER PUBLICATIONS

Chinese Office Action, serial No. 201280058471.7, dated Apr. 3, 2015, 7 pages.
(Continued)

*Primary Examiner* — Julian W Woo (57) ABSTRACT

A delivery system assembly includes an outer tube, an inner member, extending within a lumen of the outer tube, and a deflectable shaft, extending within the outer tube lumen and around the inner member; the tube and inner member are longitudinally moveable with respect to the shaft, and a distal end of the inner member is located distal to the shaft within the tube lumen. A medical device can be loaded into the tube lumen, along a distal-most portion of the tube, and contained between the inner member and a distal opening of the tube lumen. Deflecting the shaft orients the distal-most portion for navigation of the assembly, and, when the distal end of the inner member is engaged within the tube lumen, distal movement of the tube, with respect to the shaft, causes similar distal movement of the inner member and the loaded medical device toward an implant site.

9 Claims, 6 Drawing Sheets

(51) Int. Cl.
*A61N 1/375* (2006.01)
*A61N 1/362* (2006.01)
*A61N 1/05* (2006.01)

(58) Field of Classification Search
USPC .................................. 600/139, 146, 149
See application file for complete search history.

(56) References Cited

U.S. PATENT DOCUMENTS

| | | | |
|---|---|---|---|
| RE30,366 E | 8/1980 | Rasor et al. | |
| 4,245,624 A | 1/1981 | Komiya | |
| 4,676,249 A | 6/1987 | Arenas et al. | |
| 5,040,543 A | 8/1991 | Badera et al. | |
| 5,090,422 A | 2/1992 | Dahl et al. | |
| 5,147,379 A | 9/1992 | Sabbaghian et al. | |
| 5,170,803 A | 12/1992 | Hewson et al. | |
| 5,267,982 A * | 12/1993 | Sylvanowicz | A61M 25/09025 604/256 |
| 5,334,160 A | 8/1994 | Ellis | |
| 5,431,696 A | 7/1995 | Atlee, III | |
| 5,643,231 A | 7/1997 | Lurie et al. | |
| 5,662,119 A | 9/1997 | Brennen et al. | |
| 5,827,201 A | 10/1998 | Samson et al. | |
| 5,873,842 A | 2/1999 | Brennen et al. | |
| 5,951,585 A | 9/1999 | Cathcart et al. | |
| 6,074,379 A | 6/2000 | Prichard | |
| 6,102,890 A | 8/2000 | Stivland et al. | |
| 6,408,214 B1 | 6/2002 | Williams et al. | |
| 6,485,440 B1 | 11/2002 | Gardeski | |
| 6,873,870 B2 * | 3/2005 | Ferek-Petric | A61B 5/0464 600/518 |
| 7,101,361 B2 | 9/2006 | Gardeski | |
| 7,241,257 B1 | 7/2007 | Ainsworth et al. | |
| 7,369,901 B1 | 5/2008 | Morgan et al. | |
| 7,444,180 B2 | 10/2008 | Kuzma et al. | |
| 7,532,933 B2 * | 5/2009 | Hastings | A61N 1/0587 607/33 |
| 7,824,367 B2 | 11/2010 | Accisano et al. | |
| 7,840,281 B2 | 11/2010 | Kveen et al. | |
| 7,857,819 B2 | 12/2010 | Jaax et al. | |
| 7,967,798 B2 | 6/2011 | Reydel et al. | |
| 8,504,156 B2 | 8/2013 | Bonner et al. | |
| 8,721,587 B2 | 5/2014 | Berthiaume et al. | |
| 8,945,145 B2 | 2/2015 | Tran et al. | |
| 8,945,146 B2 | 2/2015 | Steingisser et al. | |
| 2002/0165537 A1 | 11/2002 | Kelley et al. | |
| 2003/0093059 A1 | 5/2003 | Griffin et al. | |
| 2003/0181855 A1 | 9/2003 | Simpson et al. | |
| 2004/0116994 A1 | 6/2004 | De Bellis | |
| 2004/0210211 A1 | 10/2004 | Devens, Jr. et al. | |
| 2005/0090834 A1 | 4/2005 | Chiang et al. | |
| 2005/0090890 A1 | 4/2005 | Wu et al. | |
| 2005/0267555 A1 | 12/2005 | Marnfeldt et al. | |
| 2005/0272975 A1 | 12/2005 | McWeeney et al. | |
| 2006/0004305 A1 | 1/2006 | George et al. | |
| 2006/0030923 A1 | 2/2006 | Gunderson | |
| 2006/0161211 A1 | 7/2006 | Thompson et al. | |
| 2006/0200221 A1 | 9/2006 | Malewicz | |
| 2006/0229698 A1 | 10/2006 | Larson et al. | |
| 2006/0241732 A1 | 10/2006 | Denker et al. | |
| 2007/0073389 A1 | 3/2007 | Bolduc et al. | |
| 2007/0088232 A1 | 4/2007 | Corradini | |
| 2007/0088418 A1 | 4/2007 | Jacobson | |
| 2007/0219551 A1 | 9/2007 | Honour et al. | |
| 2007/0250150 A1 | 10/2007 | Pal et al. | |
| 2007/0270932 A1 | 11/2007 | Headley et al. | |
| 2008/0021532 A1 * | 1/2008 | Kveen | A61N 1/362 607/115 |
| 2008/0039904 A1 | 2/2008 | Bulkes et al. | |
| 2008/0294216 A1 | 11/2008 | Jarverud et al. | |
| 2009/0005830 A1 | 1/2009 | Zhu et al. | |
| 2009/0005846 A1 | 1/2009 | Zhu et al. | |
| 2009/0069885 A1 | 3/2009 | Rahdert et al. | |
| 2009/0099641 A1 * | 4/2009 | Wu | A61F 2/95 623/1.11 |
| 2009/0182268 A1 | 7/2009 | Thielen et al. | |
| 2009/0254168 A1 | 10/2009 | Parker et al. | |
| 2010/0030294 A1 | 2/2010 | Wong et al. | |
| 2010/0198288 A1 | 8/2010 | Ostroff | |
| 2010/0204766 A1 | 8/2010 | Zdeblick et al. | |
| 2010/0274187 A1 | 10/2010 | Argentine | |
| 2011/0139754 A1 | 6/2011 | Romanowski et al. | |
| 2011/0144572 A1 | 6/2011 | Kassab et al. | |
| 2011/0251660 A1 * | 10/2011 | Griswold | A61N 1/37205 607/126 |
| 2011/0251662 A1 | 10/2011 | Griswold et al. | |
| 2012/0053651 A1 | 3/2012 | Zhu et al. | |
| 2012/0172892 A1 | 7/2012 | Gruback et al. | |
| 2012/0245665 A1 | 9/2012 | Friedman et al. | |
| 2012/0245679 A1 | 9/2012 | Solem | |
| 2013/0103047 A1 | 4/2013 | Steingisser et al. | |
| 2013/0131693 A1 | 5/2013 | Berthiaume et al. | |

FOREIGN PATENT DOCUMENTS

| | | |
|---|---|---|
| WO | WO 01/83017 A1 | 11/2001 |
| WO | WO 03/032807 A2 | 4/2003 |
| WO | WO 2006/099425 | 9/2006 |
| WO | WO 2012/092074 A1 | 7/2012 |

OTHER PUBLICATIONS

Translation of Chinese Office Action, serial No. 201280058471.7, dated Apr. 3, 2015, 5 pages.
(PCT/US2012/060015) PCT Notification of Transmittal of the International Search Report and the Written Opinion of the International Searching Authority.
English translation of Chinese Office Action, dated Nov. 24, 2015, 14 pages.
Chinese Office Action, dated Nov. 24, 2015, 9 pages, Chinese version.
Notification Concerning Transmittal of International Preliminary Report on Patentability, dated May 30, 2014, 9 pages.
PCT/US2012/065229 Notification of Transmittal of the International Search Report and the Written Opinion of the International Searching Authority, or the Declaration, dated Feb. 11, 2013, 12 pages.
PCT/US2012/056029 Notification of Transmittal of the International Search Report and the Written Opinion of the International Searching Authority, or the Declaration, dated Mar. 7, 2013, 14 pages.
(PCT/US2012/065264) PCT Notification of Transmittal of the International Search Report and the Written Opinion of the International Searching Authority, dated Jan. 4, 2013.
(PCT/US2012/049264) PCT Notification of Transmittal of the International Search Report and the Written Opinion of the International Searching Authority, dated Mar. 6, 2013.

* cited by examiner

DELIVERY SYSTEM ASSEMBLIES AND ASSOCIATED METHODS FOR IMPLANTABLE MEDICAL DEVICES

RELATED APPLICATIONS

The present application is a divisional application of U.S. patent application Ser. No. 13/279,835 (now allowed) entitled DELIVERY SYSTEM ASSEMBLIES AND ASSOCIATED METHODS FOR IMPLANTABLE MEDICAL DEVICES, filed on Oct. 24, 2011. The present application is related to the following and commonly-assigned United States patent applications: application Ser. No. 13/239,990 (now allowed) entitled DELIVERY SYSTEM ASSEMBLIES FOR IMPLANTABLE MEDICAL DEVICES, and filed on Sep. 22, 2011; and application Ser. No. 13/219,279 (now issued as U.S. Pat. No. 8,504,156) entitled HOLDING MEMBERS FOR IMPLANTABLE CARDIAC STIMULATION DEVICES, and filed on Aug. 26, 2011.

TECHNICAL FIELD

The present invention pertains to the delivery of implantable medical devices, and more particularly to system assemblies and associated methods that facilitate percutaneous transvenous deployment of relatively compact implantable cardiac medical devices.

BACKGROUND

Figure 1:
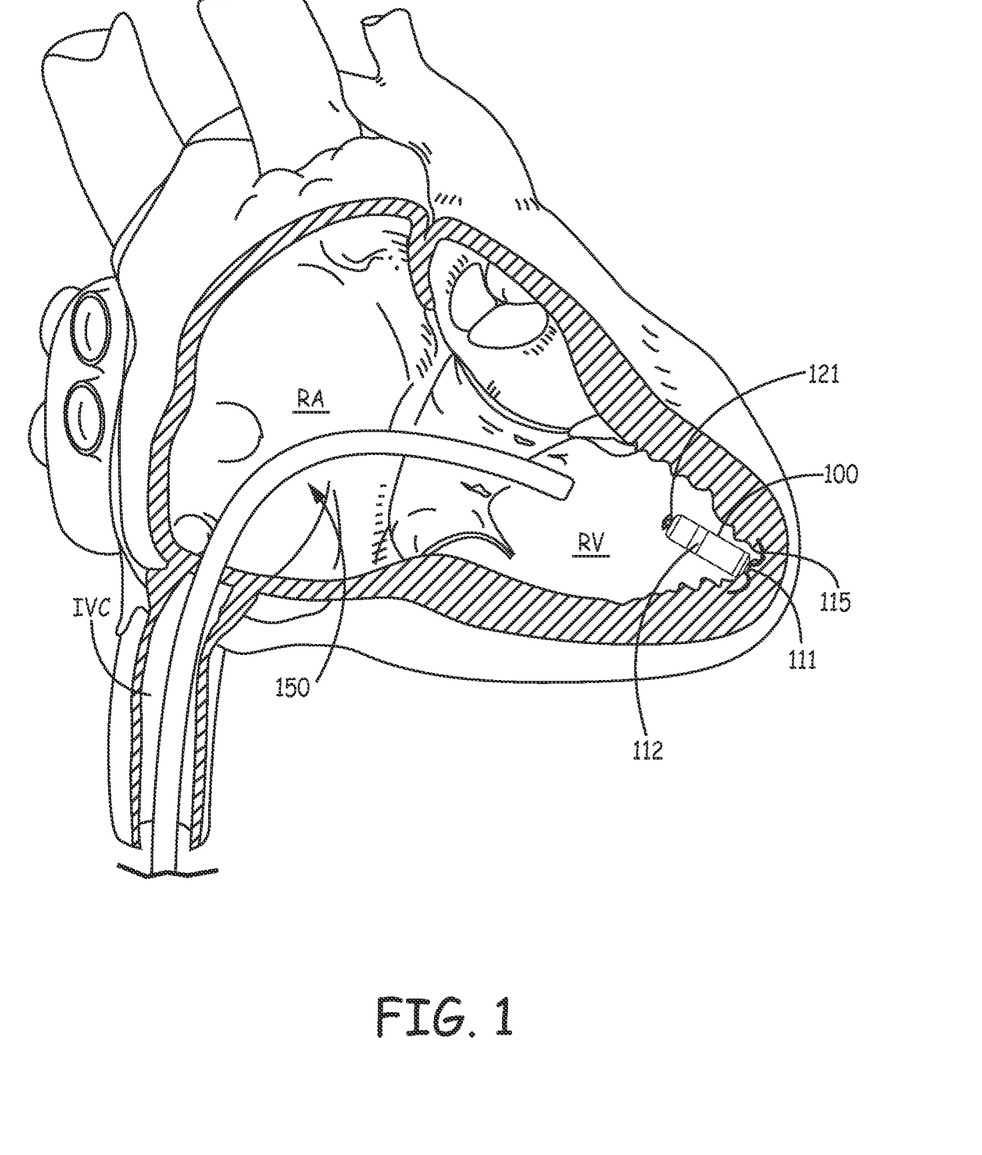
FIG. 1 is a schematic showing an example of an implanted cardiac stimulation device.

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of cardiac pacing devices that are wholly contained within a relatively compact package for implant in close proximity to the pacing site, for example, within the right ventricle (RV) of the heart. With reference to FIG. 1, such a device 100 is illustrated, wherein pace/sense electrodes 111, 112 are formed on an exterior surface of an enclosure that hermetically contains a pulse generator including pulse generator electronics and a power source. FIG. 1 illustrates a fixation member 115 mounted to an end of the enclosure of device 100, in proximity to electrode 111, in order to fix, or secure electrode 111 against the endocardial surface in the apex of the RV. The enclosure is preferably formed from a biocompatible and biostable metal such as titanium overlaid with an insulative layer, for example, medical grade polyurethane or silicone, except where electrode 112 is formed as an exposed portion of capsule 101. A hermetic feedthrough assembly (not shown), such as any known to those skilled in the art, couples electrode 111 to the pulse generator contained within the enclosure of device 100.

FIG. 1 further illustrates a distal portion of a standard guiding catheter 150 having been maneuvered up through the inferior vena cava (IVC) and into the RV from the right atrium (RA), according to methods known in the art of interventional cardiology. Although catheter 150 may be employed to deliver device 100 to the RV, for implant, more sophisticated delivery systems that facilitate improved navigation and deployment more suitable for relatively compact implantable devices, like device 100, are desired.

SUMMARY

A delivery system assembly, according to some embodiments of the present invention, includes an elongate outer tube, an elongate inner member, which extends within a lumen formed by the outer tube, and a deflectable shaft, which extends within the lumen of the outer tube and around the inner member; the outer tube and inner member are longitudinally moveable with respect to the deflectable shaft, and a distal end of the inner member is located distal to the deflectable shaft. The distal end of the inner member is preferably configured to conform to a proximal end of a medical device, and to engage within the lumen of the outer tube, in proximity to a distal opening thereof, such that an entirety of the medical device can be contained within the lumen of the outer tube, between the engaged distal end of the inner member and the distal opening of the outer tube lumen. Furthermore, when the distal end of the inner member is engaged within the lumen of the outer tube, advancement, or distal movement, of the outer tube with respect to the deflectable shaft causes similar distal movement of the inner member.

Navigation of the delivery system assembly through a venous system of a patient for deployment of the implantable medical device, according to some methods of the present invention, is facilitated by deflection of the deflectable shaft, to orient a distal-most portion of the outer tube, within which the medical device is contained/loaded, and by advancement of the outer tube with respect to the deflectable shaft, to move the distal end of the inner member, along with the contained/loaded medical device into proximity with a target implant site. Once the distal-most portion of the outer tube abuts the implant site, according to some embodiments and methods, the outer tube may be retracted with respect to the inner member in order to expose a fixation member of the medical device for engagement with tissue at the site. Some embodiments include a tether, for example, that extends within a lumen of the inner member; the tether is configured for removable attachment to the medical device, and, when attached to the medical device, may be employed to secure the device against the distal end of the inner member within the lumen of the outer tube, and/or to test the engagement of fixation member with tissue at the implant site, and/or to retain a temporary connection between the deployed medical device and the delivery system assembly, if repositioning of the deployed device is necessary.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 2A:
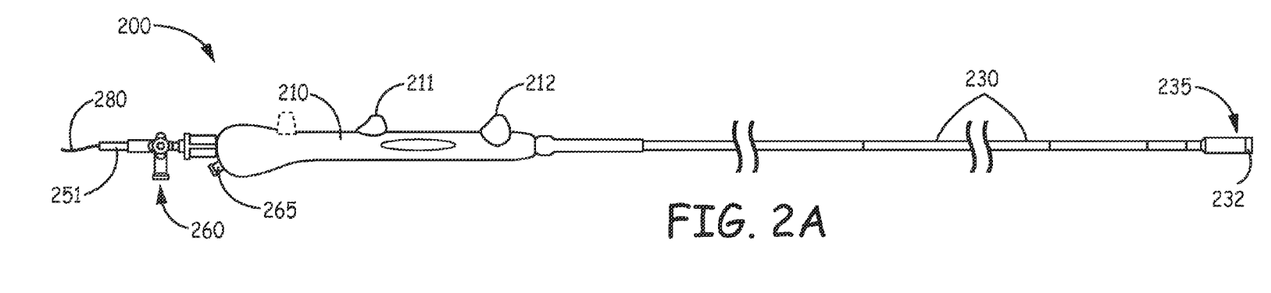
FIG. 2A is a plan view of a delivery system assembly, according to some embodiments.
Figure 2B:
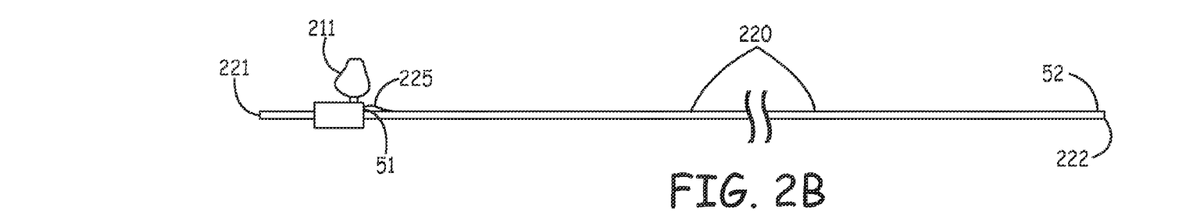
FIGS. 2B-D are plan views of middle, inner and outer subassemblies, respectively, of the system assembly shown in FIG. 2A, according to some embodiments.
Figure 2C:
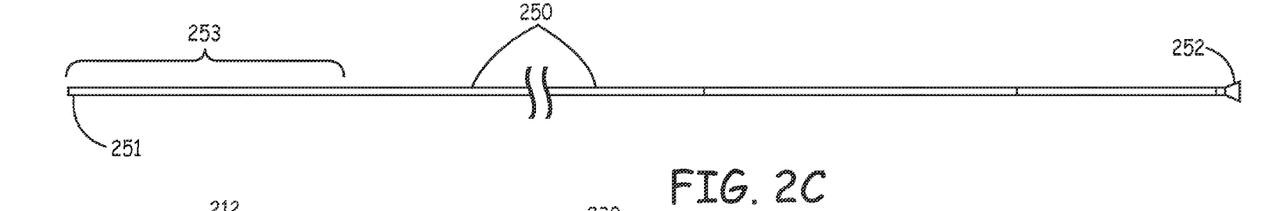
Figure 2D:
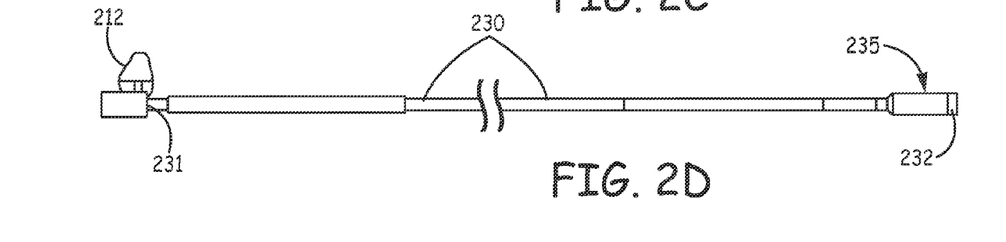

FIG. 2A is a plan view of a delivery system assembly 200, according to some embodiments; and FIGS. 2B-D are plan views of middle, inner and outer subassemblies, respectively, of system assembly 200, according to some embodiments. FIG. 2A illustrates system assembly 200 including a handle 210, which includes control member 212 and from which an elongate outer tube 230 extends; and FIG. 2D illustrates a proximal end 231 of outer tube 230 inserted within a ring of control member 212 and bonded thereto, for example, by a UV cure adhesive. According to the illustrated embodiment, outer tube 230 forms a lumen (not shown in FIGS. 2A-D) within which an elongate shaft 220, which is shown in FIG. 2B, extends; and shaft 220 includes a lumen (not shown) within which an elongate inner member 250, which is shown in FIG. 2C, extends. FIG. 2D further illustrates outer tube 230 extending from proximal end 231 to a distal-most portion 235 that is terminated by a distal end 232 of outer tube 230; and, it should be understood that, the lumen formed by outer tube 230 preferably has a proximal opening at proximal end 231 and a distal opening at distal end 232. Although FIGS. 2A and D illustrate distal-most portion 235 being enlarged from a remainder of outer tube 230, for example, having an outer diameter of approximately 0.3 inch (~0.8 cm) over a length of approximately 3.5 cm (~1.4 inch), an outer diameter along a more significant length, up to an entire length of outer tube 230, may be the same as that of the distal-most portion 235, according to some alternate embodiments. FIG. 2B illustrates shaft 220 including a proximal end 221, which is preferably fixed within handle 210 at a location proximal to proximal end 231 of outer tube 230, and a pull wire 225 that extends along a length of shaft 220 from a proximal end 51 thereof, which is coupled to a control member 211 of handle 210, to a distal end thereof 52, which is anchored in proximity to a distal end 222 of shaft 220, such that actuation of pull wire 225, via control member 211, deflects distal end 222. FIG. 2C illustrates elongate inner member 250 extending from a proximal end 251 thereof to an enlarged distal end 252 thereof; proximal end 251 of inner member 250 may extend proximally from handle 210, through a clamping mechanism 260, for example, a stop cock (FIG. 2A), which is coupled to handle 210 by a luer fitting (not shown). Alternately, proximal end 251 of inner member 250 may be contained within handle 210 and may be coupled to another, optional control member, which is shown with dashed lines in FIG. 2A. According to embodiments of the present invention, both inner member 250 and outer tube 230 are longitudinally moveable with respect to shaft 220 and with respect to handle 210.

Figure 3A:
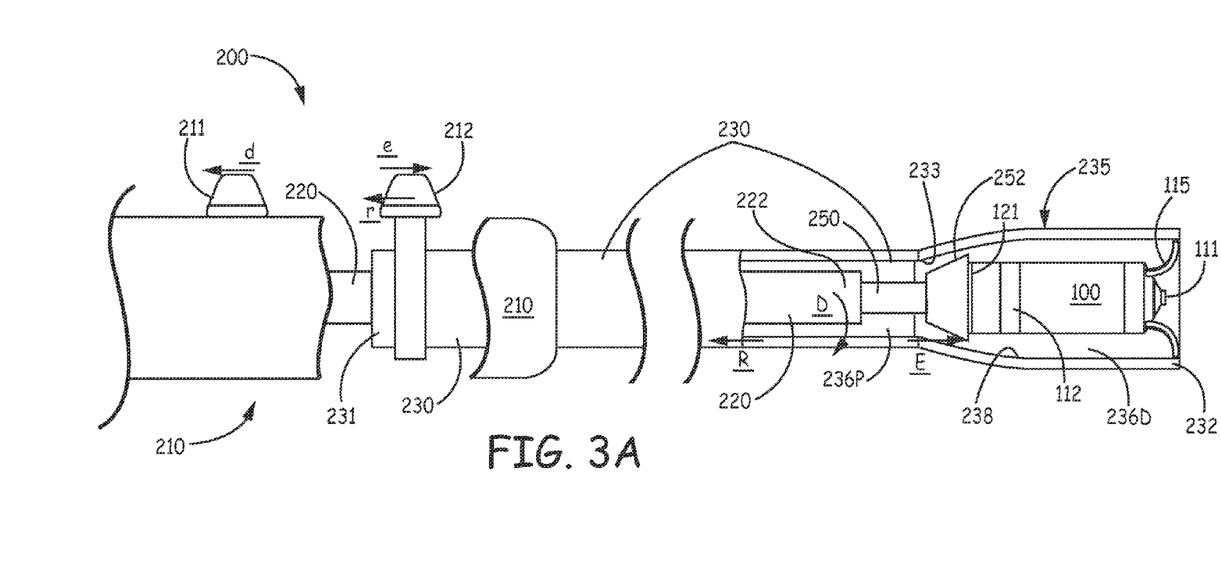
FIG. 3A is an another plan view of the delivery system assembly, including a cut-away section of an outer tube thereof, according to some embodiments.
Figure 3B:
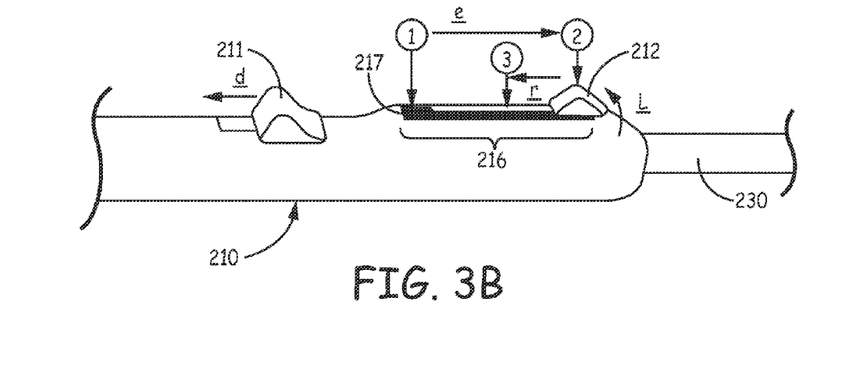
FIG. 3B is an enlarged perspective view of a portion of a handle of the assembly, according to some embodiments.

FIG. 3A is another plan view of delivery system assembly 200, according to some embodiments; and FIG. 3B is a enlarged perspective view of a portion of handle 210, according to some embodiments. FIG. 3A shows, by way of a cut-away section, a distal portion 236D of the lumen formed by outer tube 230 extending distally from an internal shoulder 233 of outer tube 230 to the distal opening of the lumen at distal end 232, and a proximal portion 236P of the lumen extending proximally from shoulder 233. FIG. 3A illustrates a distal end 222 of shaft 220 located within lumen proximal portion 236P, just proximal to lumen distal portion 236D where enlarged distal end 252 of inner member 220 is engaged. According to the illustrated embodiment, when control member 211 is moved per arrow d to draw on pull wire 225 of shaft 220, distal end 222 of shaft 220 is deflected so that inner member 250 and outer tube 230 are likewise deflected per arrow D. FIG. 3A further illustrates distal end 252 of inner member 250 engaged within lumen 236D of distal-most portion 235 of outer tube 230 by a confronting, or abutting interface with shoulder 233, so that when control member 212 is moved distally, for example, from a first, most proximal position 1 toward a second position 2, per arrow e (FIG. 3B), outer tube 230 and inner member 250 are moved together distally, per arrow E, with respect to shaft 220. FIG. 3B illustrates a slot 216 of handle 210, along which control member 212 is slidable, including a locking notch 217 at first position 1 and control member engaged in a similar locking notch at second position 2. According to the illustrated embodiment, control member 212 is laterally moveable, per arrow L, into locking engagement with notches 217, to prevent inadvertent extension or retraction of outer tube 230, from the respective positions corresponding to opposite ends of travel along slot 216. With further reference to FIGS. 3A-B, when control member 212 is moved toward a third position 3, per arrow r, outer tube 230 is retracted, or moved proximally, per arrow R, with respect to shaft 220, and distal end of inner member 250 is disengaged from distal-most portion 235, so that the proximal movement of outer tube 230 may be independent of, or relative to inner member 250. It should be noted that another locking notch 217 for control member 212 may be located at third position 3, according to some embodiments, to retain outer tube 230 in the retracted position. According to some alternate embodiments and methods, with reference to FIG. 2A, proximal end 251 of inner member 250 may be pushed to advance distal end 252 out from distal-most portion 235 of outer tube 230, either independently of or in conjunction with outer tube retraction. In order to facilitate the relative movement of outer tube 230 and inner member 250, a biocompatible lubricant, such as MED 361 silicone oil, may be applied between the outer surface of enlarged distal end 252 of inner member and an inner surface 238 of distal-most portion 235 of outer tube 230. According to some embodiments, an O-ring type seal member (i.e. silicone; not shown), which may be lubricated, for example, with silicone oil, forms a dynamic sealing interface between outer tube 230 and shaft 220 within handle 210, in proximity to control member 212. Another lubricated O-ring type seal member may also be located between inner member 250 and shaft, in proximity to control member 211, for similar dynamic sealing therebetween. (It should be noted that alternate embodiments may employ other means of similar engagement between distal end 252 of inner member 250 and lumen 236D that allows for the above-described coordinated distal movement of outer tube 230 and inner member 250 and the independent proximal movement of outer tube 230, or independent distal movement of inner member 250.)

According to some preferred embodiments, enlarged distal end 252 of inner member 250 conforms to a proximal end 121 of device 100, and, with reference to FIG. 3, when distal end 252 is engaged within lumen 236D, device 100 is wholly contained within distal-most portion 235 of outer tube 230, between distal end 252 and distal end 232. According to an exemplary embodiment, lumen 236D has a maximum diameter of approximately 0.275 inch (~0.7 cm) that extends along a length of approximately 3 cm to contain device 100. According to some embodiments, the conforming configuration of distal end 252 can help to retain device 100 within distal-most portion 235 of outer tube 230 during navigation of delivery system assembly 200 and prior to deployment of device 100 therefrom. An outer surface of enlarged distal end 252 may form a seal against an inner surface 238 of distal-most portion 235, for example to prevent blood ingress within the lumen of outer tube 230 during navigation of assembly 200; however, according to some preferred embodiments, a gap between distal end 252 and inner surface 238 of distal-most portion 235 allows fluid, for example, saline, to be flushed around device 100 (loaded within distal-most portion 235) and thereby prevent the introduction of air into a patient's venous system as delivery system assembly 200 is inserted therein. With reference back to FIG. 2A, the fluid may be introduced through a port 265 of handle 210, which is in fluid communication with the lumen (proximal portion 236P-FIG. 3) of outer tube 230.

Figure 4A:
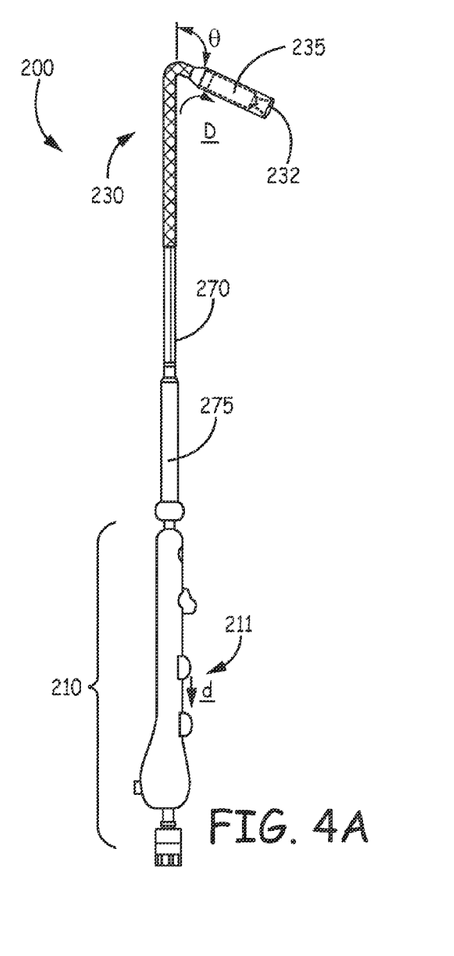
FIGS. 4A-C are plan views of the delivery system assembly in various states of articulation, according to some embodiments.
Figure 4B:
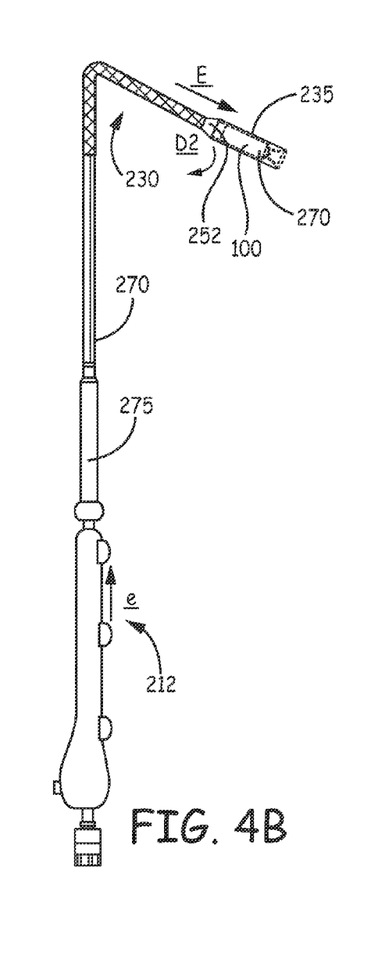
Figure 4C:
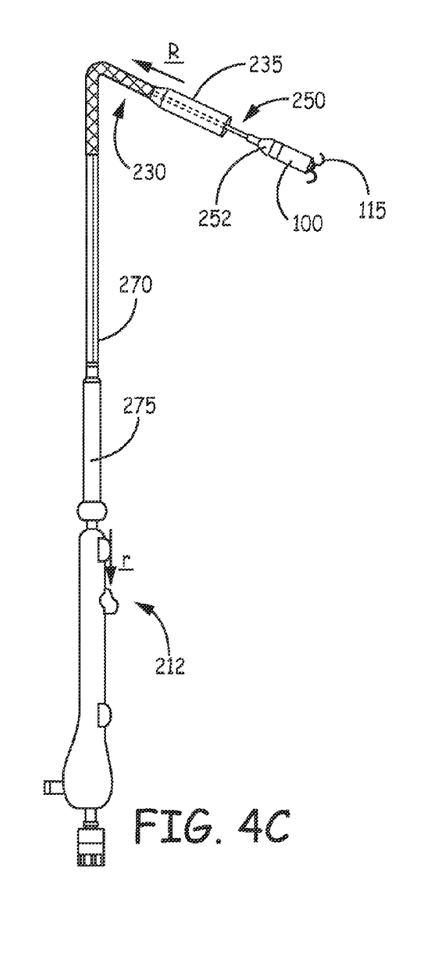

FIGS. 4A-C are plan views of delivery system assembly 200 in various states of articulation, according to some embodiments, as facilitated by the various elements of assembly 200, introduced above. FIG. 4A illustrates the above-described deflection, per arrow D, actuated by movement of control member 211 to draw pull wire 225 per arrow d; the deflection helps to orient distal-most portion 235 of outer tube 230 for navigation within a patient's venous system, for example, as described in greater detail below. An angle θ of the deflection (from the vertical line of FIG. 4A) may range from approximately 100 degrees to approximately 200 degrees. FIG. 4B illustrates an extension of system assembly 200, per arrow E, actuated by movement of control member 212 per arrow e to push/advance outer tube 230, along with inner member 250, distally, as described above; the extension provides a variable reach of distal-most portion 235 of outer tube 230 in order to deploy device 100, carried therein, to a target implant site, for example, as described below. The range of reach facilitated by the extension may be from approximately 5 cm to approximately 10 cm. As described above, in conjunction with FIG. 3B, control member 212, when positioned at each end of the range of reach for outer tube 230, is preferably locked within the corresponding locking notch 217. FIG. 4C illustrates the above-described retraction of outer tube 230, per arrow R, which is also actuated by movement of control member 212, but in an opposite direction, per arrow r. When distal end 232 of outer tube 230 reaches the target implant site, retraction of outer tube 230 exposes fixation member 115 of device 100 to engage tissue at the site. According to some preferred embodiments, distal end 252 of inner member 250 is radiopaque and distal end 232 of outer tube 230 is fitted with a radiopaque marker, so that the retraction of outer tube 230, relative to distal end 252, for the deployment of device 100, can be observed via fluoroscopy. According to an exemplary embodiment, enlarged distal end 252 is formed from a polyether block amide, for example, PEBAX® 7033, with a radiopaque Barium sulfate filler, and distal-most portion 235 is also formed from a polyether block amide, for example, PEBAX® 7233, which, at distal end 232, includes a radiopaque band of 75% Tungsten and 25% PEBAX® 6033 sandwiched between layers of the PEBAX® 7233.

The above-described conforming configuration of distal end 252 of inner member 250 may help to retain a temporary connection between device 100 and assembly 200 until fixation member 115 becomes engaged with the tissue, but, according to some preferred embodiments, device 100 is further secured to assembly 200 by a tether 280 (FIGS. 2A and 6), which is configured for removable attachment to proximal end 121 of device 100, as will be described in greater detail below. Tether 280 is preferably formed from a thinly stranded polymer or fiber, such as braided polyethylene terephthalate (PET) or monofilament polypropylene. Although FIG. 4C illustrates, distal end 252 of inner member 250 positioned distal to distal-most portion 235 of outer tube 230, in some alternate embodiments, the relative movement of outer tube 230 and inner member 250 is limited such that distal end 252 of inner member 250 cannot be positioned distal to/outside of distal-most portion 235 of outer tube 230.

A flexibility of each of shaft 220 and outer tube 230, is preferably graduated from a relatively stiff proximal segment to a relatively flexible distal segment in order to facilitate the deflection, per arrow D (FIGS. 4A-C), and may be of any suitable construction known in the art. According to an exemplary embodiment, outer tube 230 includes: a proximal segment, which is formed by a stainless steel braid (i.e. 0.0018"×0.008"×45 PPI) embedded between a PEBAX® 6333 liner and a PEBAX® 7033 outer jacket, and which extends over a length of approximately 102 cm (a proximal portion of which length is always contained within handle 210); and a distal segment, which is also formed by the same aforementioned liner and braid, but has an outer jacket of PEBAX® 3533, and which extends distally from the proximal segment, over a length of approximately 10 cm, to distal-most portion 235. Outer and inner diameters of outer tube 230, along the above-described segments, may be approximately 0.187 inch (~4.75 mm) and approximately 0.154 inch (~3.91 mm), respectively. Shaft 220, according to the same exemplary embodiment, preferably includes a polytetrafluoroethylene (PTFE) liner overlaid with a 304 stainless steel braid (0.001"×0.005"; 65 pics per inch), along which a PTFE tubing, that forms a lumen for pull wire 225 (i.e. 0.010" stainless steel wire), is threaded; a proximal segment of shaft 220, which is approximately 122 cm long (including that portion which extends within handle 210), has a PEBAX® 7233 outer jacket; an intermediate segment of shaft 220, which extends distally from the proximal segment over a length of approximately 2.5 cm, has a PEBAX® 3533 outer jacket; and a distal segment, which terminates shaft 220 and in which pull wire 225 is anchored, has a length of approximately 0.3 cm and a PEBAX® 7233 outer jacket. Inner and outer diameters of shaft 220, along the above-described segments, may be approximately 0.068 inch (~1.73 mm) and approximately 0.118 inch (~3 mm), respectively. Furthermore, according to the exemplary embodiment, a shaft of inner member 250, which extends proximally from distal end 252, for example, over a length of approximately 130 cm, includes a 304 stainless steel braid (0.002" double stranded; 40 pics per inch) sandwiched between a liner and an outer layer, each of which is formed from Rilsan® AESNO (Polyamide 12), with 30% bismuth subcarbonate. Inner and outer diameters of the shaft of inner member 250 may be approximately 0.0415 inch (~1.05 mm) and approximately 0.058 inch (~1.47 mm), respectively, with distal end 252 preferably enlarged therefrom, as described above, for example, to engage within distal-most portion 235 of outer tube 230 and/or to conform to proximal end 121 of device 100. With reference back to FIG. 2C, a proximal length 253 of inner member 250 preferably include a stainless steel hypo-tube, for example, to support the above described shaft of inner member 250 for pushability and manipulation of inner member 250. The hypo-tube may have an inner diameter of approximately 0.025" (~0.6 mm) and an outer diameter of approximately 0.040" (~1 mm), extend within the shaft of inner member 250, for example, over a length of approximately 15 cm, and extend proximally from the shaft, for example, over a length of approximately 15 cm, to terminate at proximal end 251 of inner member 250.

Figure 5:
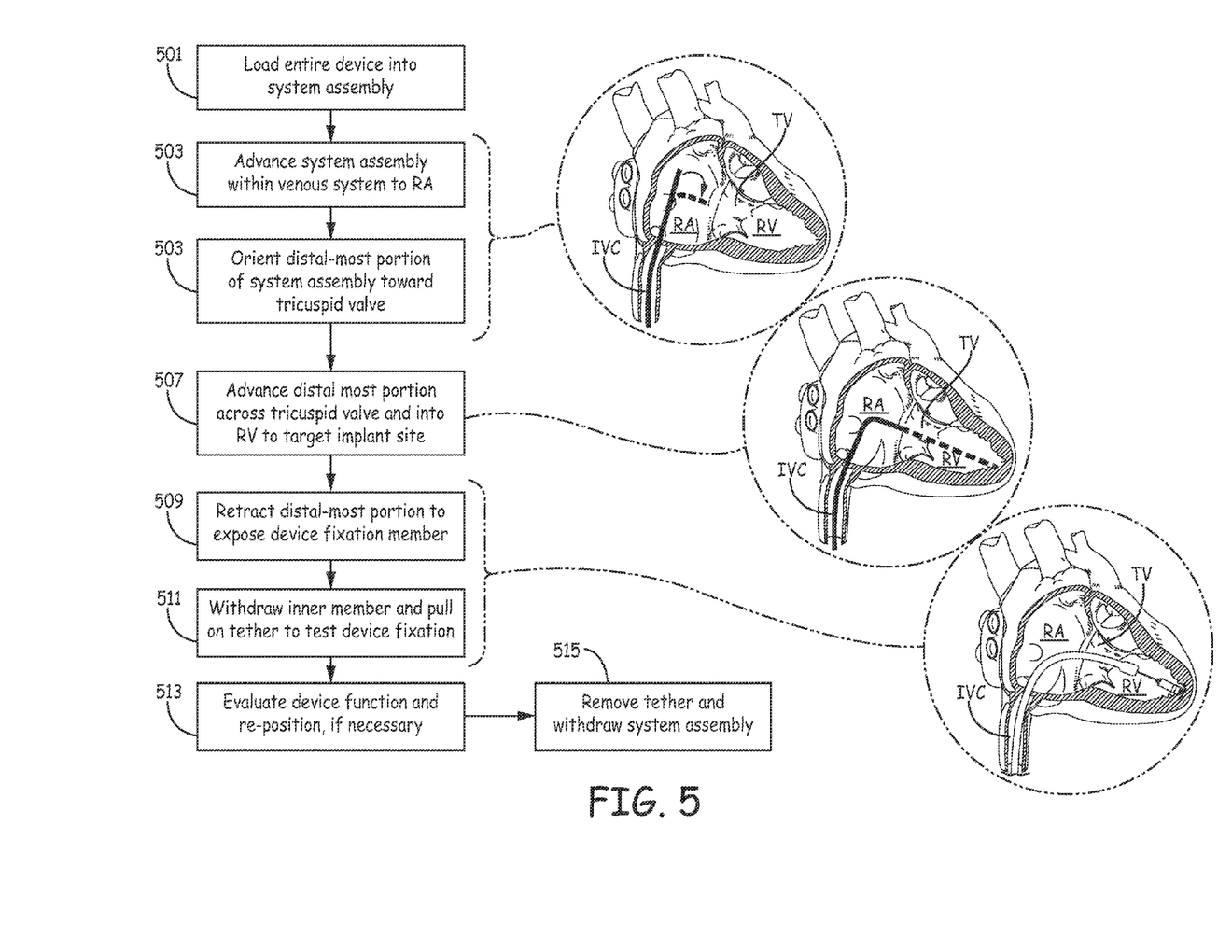
FIG. 5 is a flow chart, including some schematics, that outlines some methods of the present invention.
Figure 6:
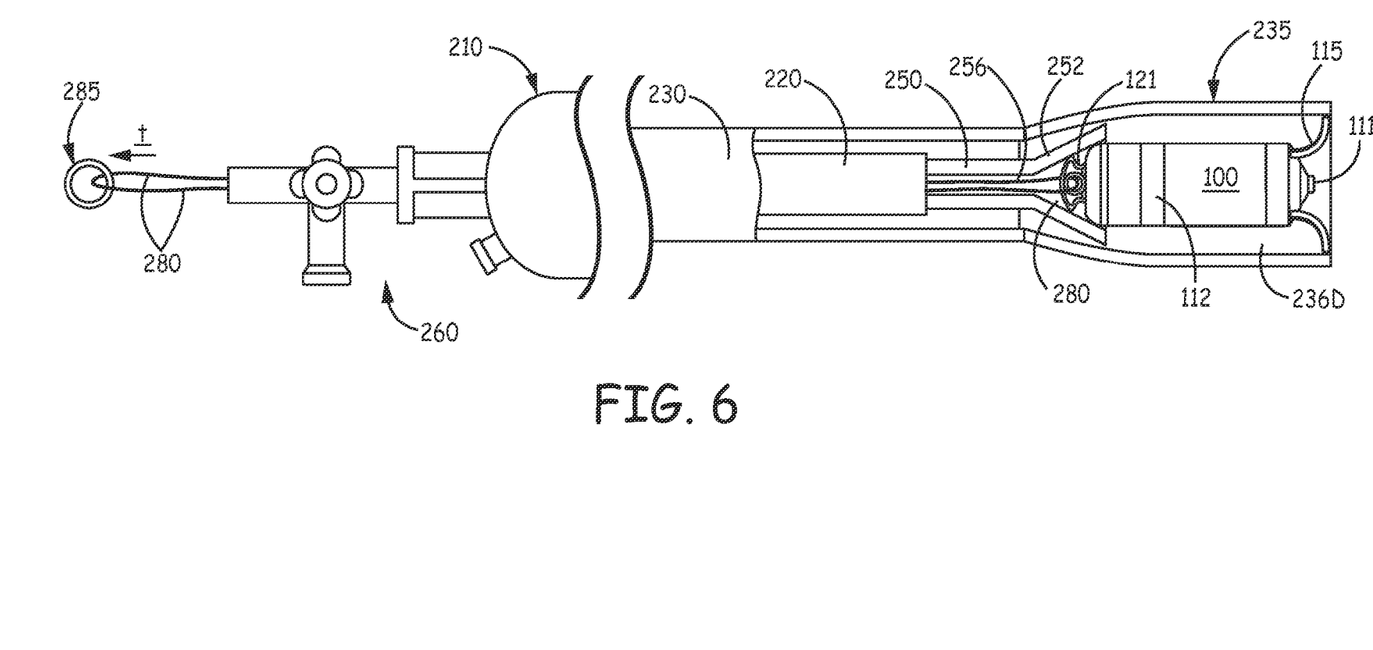
FIG. 6 is a plan view of the delivery system assembly, including a cross-section view of a distal portion thereof, according to some embodiments that include a tether.

FIG. 5 is a flow chart, including some schematics, that outlines some methods of the present invention for deploying an implantable cardiac medical device, such as device 100. According to an initial step 501, and with reference to FIG. 3A, device 100 is loaded into distal portion 236D of the lumen formed by outer tube 230 of delivery system assembly 200, such that an entirety of device 100 is contained within distal-most portion 235 of outer tube 230 and proximal end 121 of device 100 abuts distal end 252 of inner member 250. According to some preferred embodiments and methods, when loading device 100, per step 501, a tether, for example, tether 280 (described below, in conjunction with FIG. 6) is attached to proximal end 121 of device 100; the tether preferably extends proximally from device 100, for example, through a lumen of inner member 250 and proximally from proximal end 251 (FIGS. 2A and 6). The above-referenced co-pending and commonly assigned U.S. patent application Ser. No. 13/219,279 describes some alternate configurations of proximal end 121 of device 100 that may be employed for tether attachment.

After loading device 100, air may be purged from delivery system assembly 200 by flushing the lumens of inner member 250, shaft 220 and outer tube 230; then, as positive fluid pressure is held within the lumens, delivery system assembly 200 is introduced into a patient's venous system, for example, through an introducer sheath at a femoral site, so that delivery system assembly 200 may be advanced, per step 503, into the RA (right atrium) of the heart, for example, via the IVC (inferior vena cava), at which point, distal-most portion 235 of outer tube 230 is oriented toward the tricuspid valve (TV), per step 505. According to preferred methods, distal-most portion 235 is oriented by deflecting distal end 222 of shaft 220, via control member 211 and pull wire 225, as described above. With reference back to FIG. 4A, angle θ may be approximately 110 degrees to orient distal-most portion 235 toward the TV. Once oriented, distal-most portion 235 of outer tube 230 is advanced across the TV, into the RV (right ventricle), and to a target implant site, per step 507, such that distal-most portion 235 abuts the site and the distal opening of the lumen of outer tube 230, at distal end 232, is within tissue, for example, trabeculae carneae, at the site. As described above, control member 212 is preferably employed to actuate the advancement/extension of outer tube 230, and the engagement of enlarged distal end 252 of inner member 250 causes inner member 250 and device 100 to be advanced along with distal-most portion 235, while shaft 220 remains relatively stationary. Subsequently, distal-most portion 235 is retracted, per step 509, with respect to distal end 252 of inner member 250, so that fixation member 115 of device 100 is exposed to engage with the tissue at the site. The advancement and retraction of distal-most portion 235 may be actuated by distal and proximal movement of control member 212, which is coupled to proximal end 231 of outer tube 230, as described above. According to alternate methods, inner member 250 may be advanced relative to outer tube 230 to push device 100 distally and thereby expose fixation member 115, however the retraction of distal-most portion 235, per step 509, is the preferred means to expose fixation member 115, so as to prevent injury, for example, perforation by excess push force, at the target implant site.

According to some embodiments, outer tube 230 may be rotatable, with respect to handle 210, about a longitudinal axis thereof, such that, according to some methods, following the above-described deflection of shaft 220, per step 505, oriented distal-most portion 235 may be swept in an arc to further enable navigation from the RA into the RV and/or within the RV to one or more target implant sites, according to step 507. Alternately shaft 220 may be rotatable with respect to handle 210 toward the same purpose. It is contemplated that the above-described control members 212 and 211, which correspond to outer tube 230 and shaft 220, respectively, may be configured to also actuate the respective rotation. Furthermore, according to some embodiments, an additional degree of freedom for deflection of delivery system assembly may be provided by an additional pull wire, either integrated into outer tube 230 or into inner member 250. For example, inner member 250 may be formed by a dual lumen shaft, wherein the pull wire (not shown) extends along a length of a second lumen (not shown) that extends alongside lumen 256. A proximal end of the additional pull wire may be coupled to a third control member of handle 210 (for example, like the optional control member shown with dashed lines in FIG. 2A), and a distal end of the additional pull wire may be anchored in proximity to enlarged distal end 252 of inner member 250, so that an additional deflection, distal to that per arrow D in FIG. 4A, may be actuated, for example, per arrow D2 of FIG. 4B. The above-referenced related, co-pending and commonly assigned U.S. patent application Ser. No. 13/239,990 describes such an inner member (inner member 220), the description of which is hereby incorporated by reference. Such a dual lumen construction for inner member 250 may necessitate a larger shaft 220, for example, one having an inner diameter of approximately 0.128 inch and an outer diameter of approximately 0.142 inch.

With reference back to FIGS. 4A-C, an optional relatively rigid sheath 270 is shown extending distally from handle 210 over a limited length of outer tube 230. Optional sheath 270 facilitates the above-described extension and retraction, for example, by preventing an operator who is handling delivery system 200 from inadvertently applying a force around outer tube 230 in proximity to handle 210, which force could impede the extension and retraction. The above-referenced co-pending and commonly assigned related U.S. patent application Ser. No. 13/239,990 describes such a sheath (stability sheath 250), as well as an optional overlay, which is also shown in FIGS. 4A-C and designated by reference numeral 275, the descriptions of which are hereby incorporated by reference. With further reference to FIGS. 4A-C, optional overlay 275 surrounds outer tube 230 in proximity to handle 210. Optional overlay 275 can facilitate the above-described extension and retraction, for example, by providing an enhanced interface between system assembly 200 and a valve of the aforementioned introducer sheath, for example, an interface that provides improved sealing and/or additional radial strength to counteract a compressive force of the valve, which, if the valve is a Tuohy Borst type, can be tightened down around system 200 to different degrees depending upon the operator. Optional overlay 275 is preferably slidable over outer tube 230 so that overlay 275 may be repositioned with respect to handle 210 in order to coincide with the valve of the introducer sheath, prior to step 507.

Returning now to FIG. 5, after exposing fixation member 115 of device 100, per step 509, inner member 250 is withdrawn, or moved away from device 100, but, according to preferred embodiments and methods, a tether, like tether 280 of FIG. 6, retains a temporary connection between device 100 and delivery system assembly 200 until acceptable function of device 100 at the implant site is verified. Inner member 250 is preferably withdrawn relative to outer tube 230 so as to retract enlarged distal end 252 back into engagement within lumen distal portion 236D. According to step 511, once inner member 250 is withdrawn, a tug force is applied to the proximal end of tether 280 to test adequate fixation of device 100 at the site, and if fixation is verified, the function of device 100 is evaluated, per step 513. According to the embodiment of device 100 that is illustrated in FIGS. 1, 3A and 6, electrical pacing stimulation and sensing, via electrodes 111, 112, is evaluated as part of the function of device 100; other aspects of device function that may be evaluated include, without limitation, telemetry signal strength for wireless communications and the quality of other types of sensing, for example, if included in device 100, by testing the performance of a mechanical transducer and/or chemical sensor.

If the evaluated function of the implanted device 100 is not acceptable, repositioning of device 100 to another target implant site is undertaken, per step 513. Repositioning may be accomplished by re-advancing distal-most portion 235 of outer tube 230 together with engaged distal end 252 of inner member 250, over the tether and back to device 100, while pulling on tether to remove any slack, so as to 'recapture' or re-load device 100 into distal-most portion 235 through the distal opening of the lumen at distal end 232. As distal-most portion 230 is moved over device 100, distal end 232 preferably disengages fixation member 115 from the tissue so that an entirety of device 100 is contained within distal-most portion 235 for repositioning of delivery system assembly 200. Repositioning delivery system assembly 200 may be accomplished by adjusting the deflection of shaft 220 to re-orient distal-most portion 235, with or without adjusting the amount of extension of outer tube 230 with respect to shaft 220 (i.e. per arrow E of FIG. 4B), and/or by other manipulations of system assembly 200, for example, the rotation of outer tube 230 or shaft 220 and/or additional deflection of outer tube 230 or inner member 250, as described above for some alternate embodiments. Once assembly 200 is repositioned at another target site, device 100 may be re-deployed, for example, according to steps 509 and 511. It should be noted that navigation of system assembly 200 and the deployment of device 100 may be monitored via fluoroscopy, and, as indicated above, distal end 252 of inner member 250 and distal end 232 of outer tube are preferably radiopaque for fluoroscopic visualization. Finally, when the function of device 100 is found to be acceptable, either at the initial target implant site, or at an alternate implant site, the tether is removed from device 100 through system assembly 200, and system assembly 200 is withdrawn from the venous system, per step 515. FIG. 6 is a plan view of the delivery system assembly, including a cross-section view of a distal portion thereof, according to some embodiments that include tether 280, for reference in conjunction with further detailed description of some above-described method steps.

FIG. 6 illustrates inner member 250 including a lumen 256 that extends along a length thereof, from a proximal opening at proximal end 251 (FIGS. 2A and 2C) to a distal opening at enlarged distal end 252, and a loop of tether 280 extending along a length of lumen 256. Tether 280 is shown threaded through an eyelet formed in proximal end 121 of device 100, such that a distal portion of the tether loop is located within distal end 252 of inner member. FIG. 6 further illustrates a proximal end of tether loop extending proximally from handle 210, through clamping mechanism/stop cock 260, and terminated by a handling feature 285 in which opposite terminal ends of tether 280 are engaged. According to some methods, when device 100 is loaded into system assembly 200, per step 501 of FIG. 5, tether 280 is attached to proximal end 121 of device 100, and then terminal ends of tether 280 are pulled through lumen 256 of inner member 250, from distal end 252 and out through handle 210, for example, by an elongate needle-like tool (not shown). The loop of tether 280 is then formed by engaging the terminal ends in handling member 285 as shown in FIG. 6. According to some embodiments, when tether 280 is pulled taught, per arrow t, handling member 285 may be secured in a feature of handle 210 (not shown), and thereby secure proximal end 121 of device 100 against a confronting surface of distal end 252 of inner member 250. Alternately, as shown in FIG. 6, clamping mechanism/stop cock 260 is employed to secure tether 280 once pulled taught. Device 100 may remain thus secured by tether 280 throughout steps 503 to 509 until inner member 250 is withdrawn, per step 511, then, when the function of device 100 is evaluated, per step 513, some slack in tether 280 is desirable to prevent tether 280 from applying any pull force on the implanted device. Following evaluation, if device 100 needs to be repositioned to an alternate implant site, the slack is removed from tether 280 as distal-most portion 235 of outer tube 230, together with engaged distal end 252 of inner member 250, are advanced back toward device 100, over tether 280, to re-capture device 100. Finally, when the function of device 100 is found to be acceptable, either at the initial or alternate target implant site, tether 280 is removed from device 100 through system assembly 200 by releasing one of the terminal ends from handling member 285, for example, by cutting into the tether loop, and pulling on the other end of tether 280, which is still engaged by handling member 285, to draw tether 280 proximally out from lumen 256 of inner member 250.

In the foregoing detailed description, the invention has been described with reference to specific embodiments. However, it may be appreciated that various modifications and changes can be made without departing from the scope of the invention as set forth in the appended claims.

We claim:

1. A method for deploying an implantable cardiac medical device, the method comprising:
   loading an entirety of the implantable medical device into a distal-most portion of an outer tube of a delivery system assembly such that a proximal end of the medical device abuts a distal end of an inner member of the delivery system assembly, the inner member extending within a lumen formed by the outer tube;
   advancing the delivery system assembly within a venous system of a patient to locate the distal-most portion of the outer tube, with the medical device loaded therein, within a right atrium of the patient;

orienting the located distal-most portion of the outer tube toward a tricuspid valve of the patient by deflecting a distal end of a shaft of the delivery system assembly independently of the outer tube and the inner member, the shaft extending within the lumen of the outer tube and around the inner member such that the distal end of the shaft is positioned proximal to the distal end of the inner member;

advancing, with respect to the deflected distal end of the shaft, the distal-most portion of the outer tube through the tricuspid valve and into a right ventricle of the patient to a target implant site, such that the distal-most portion of the outer tube abuts the implant site, the advancing carrying the distal end of the inner member and the loaded medical device along with the distal-most portion, by means of an engagement of the distal end of the inner member within the lumen of the outer tube; and retracting the outer tube with respect to the distal end of the inner member and the shaft to expose a fixation member of the medical device for engagement of tissue at the implant site.

2. The method of claim 1, further comprising:

attaching a tether to the proximal end of the implantable medical device when loading the device into the distal-most portion of the delivery system assembly;

threading the tether through a lumen of the inner member such that terminal ends of the tether are accessible at a proximal end of the delivery system assembly;

withdrawing the inner member along the tether and away from the medical device, after retracting the outer tube; and tugging on the tether to test engagement of the fixation member of the medical device, after withdrawing the inner member.

3. The method of claim 2, further comprising:

evaluating engagement of the fixation member of the device by tugging on the proximal portion of the tether; and responsive to the evaluated engagement of the fixation member not being acceptable, re-loading the device into the distal-most portion of the outer tube of the delivery system assembly by:

advancing the inner member back toward the medical device so that the proximal end of the device abuts the distal end of the inner member while pulling on the proximal portion of the tether to remove any slack in the tether; and advancing the outer tube over the shaft and the inner member until both the distal end of the inner member and an entirety of the medical device are contained within the distal-most portion of the outer tube; and repositioning the delivery system assembly and the re-loaded medical device such that the distal-most portion of the outer tube abuts another target implant site.

4. The method of claim 3, wherein the repositioning comprises re-orienting the distal-most portion of the outer tube of the delivery system assembly by adjusting the deflection of the shaft of the delivery system assembly.

5. The method of claim 3, further comprising deflecting the inner member, in proximity to the distal end thereof, the deflecting of the inner member to further orient the distal-most portion of the outer tube prior to, or in conjunction with, advancing the distal-most portion to the target implant site or to the other target implant site.

6. The method of claim 3, further comprising rotating the outer tube to further orient the distal-most portion of the outer tube prior to, or in conjunction with, advancing the distal-most portion to the target implant site or to the other target implant site.

7. The method of claim 1, further comprising deflecting the inner member, in proximity to the distal end thereof, the deflecting of the inner member to further orient the distal-most portion of the outer tube prior to, or in conjunction with, advancing the distal-most portion to the target implant site.

8. The method of claim 1, further comprising rotating the outer tube to further orient the distal-most portion of the outer tube prior to, or in conjunction with, advancing the distal-most portion to the target implant site.

9. The method of claim 1, further comprising positioning an overlay of the delivery system to coincide with a valve of an introducer sheath through which the delivery system assembly is advanced, after advancing the delivery system assembly within the venous system and prior to advancing the distal-most portion of the outer tube through the tricuspid valve, the overlay being slideable over the outer tube and, when positioned, providing an enhanced interface between the valve of the introducer sheath and the delivery system assembly.

* * * * *